United States Patent
Burggraf et al.

(10) Patent No.: US 9,431,141 B1
(45) Date of Patent: Aug. 30, 2016

(54) RECONFIGURABLE LIQUID ATTENUATED COLLIMATOR

(71) Applicants: Larry W Burggraf, Dayton, OH (US); Benjamin R Kowash, Livermore, CA (US); Jack G. M. FitzGerald, Arlington, VA (US)

(72) Inventors: Larry W Burggraf, Dayton, OH (US); Benjamin R Kowash, Livermore, CA (US); Jack G. M. FitzGerald, Arlington, VA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 145 days.

(21) Appl. No.: 14/210,581

(22) Filed: Mar. 14, 2014

Related U.S. Application Data (60) Provisional application No. 61/817,567, filed on Apr. 30, 2013.

(51) Int. Cl.
| | |
|---|---|
| *G21K 1/00* | (2006.01) |
| *G21K 1/04* | (2006.01) |
| *A61B 6/06* | (2006.01) |

(52) U.S. Cl.
CPC .............. *G21K 1/04* (2013.01); *G21K 1/046* (2013.01); *A61B 6/06* (2013.01)

(58) Field of Classification Search
CPC ........ A61B 6/06; A61B 6/4035; G01T 1/29; G01T 1/2914; G01T 1/295; G21K 1/02; G21K 1/025; G21K 1/04; G21K 1/043; G21K 1/046; G21K 1/10; G21K 1/12
See application file for complete search history.

(56) References Cited

U.S. PATENT DOCUMENTS

| | | | | |
|---|---|---|---|---|
| 4,446,570 | A * | 5/1984 | Guth ................ | G21K 1/025 250/363.1 |
| 4,856,042 | A * | 8/1989 | Staron .............. | G21K 1/04 378/147 |
| 5,606,165 | A | 2/1997 | Chiou et al. | |
| 5,625,665 | A * | 4/1997 | Fokkink ............ | G21K 1/10 378/156 |
| 5,966,426 | A * | 10/1999 | Marra .............. | G21K 1/10 378/156 |
| 6,118,855 | A * | 9/2000 | Welters ............ | G01N 23/04 378/156 |
| 6,188,749 | B1 * | 2/2001 | Schiller ............ | G21K 1/10 378/156 |
| 6,275,568 | B1 * | 8/2001 | Prins .............. | G21K 1/10 378/156 |

(Continued)

FOREIGN PATENT DOCUMENTS

| | | |
|---|---|---|
| EP | 0920643 B1 | 6/2003 |

*Primary Examiner* — Thomas R Artman
(74) *Attorney, Agent, or Firm* — AFMCLO/JAZ; Jason Sopko

(57) ABSTRACT

A reconfigurable radiographic aperture mask collimator apparatus includes a body portion configured to receive an attenuating liquid having a first attenuation value per unit volume. The apparatus further includes a grid portion mated to a face of the body portion and a plurality of passageways each having a cross sectional area and a length. The plurality of passageways is disposed within the grid portion. A plurality of plugs is slidably disposed within the plurality of passageways, and each of the plurality of plugs has a second attenuation value per unit volume less than the first attenuation value. One of the plurality of passageways is filled with a column of attenuating liquid that is coincident with an end of the one of a plurality of plugs contained therein, and wherein the column substantially conforms to the cross sectional area.

1 Claim, 4 Drawing Sheets

(56) References Cited

U.S. PATENT DOCUMENTS

| | | | |
|---|---|---|---|
| 6,370,228 B1 * | 4/2002 | Mockler | G21K 1/10 378/156 |
| 6,426,999 B2 * | 7/2002 | Prins | G21K 1/10 378/156 |
| 6,611,578 B2 * | 8/2003 | Snoeren | G21K 1/10 378/156 |
| 6,836,535 B2 * | 12/2004 | Toth | A61B 6/032 378/156 |
| 7,272,208 B2 * | 9/2007 | Yatsenko | A61B 6/032 378/145 |
| 7,400,434 B2 * | 7/2008 | Brahme | G21K 1/046 359/237 |
| 7,489,764 B2 * | 2/2009 | Ein-Gal | A61N 5/1042 378/150 |
| 7,888,626 B2 | 2/2011 | Slinger et al. | |
| 7,915,591 B2 | 3/2011 | Zelakiewicz et al. | |
| 8,971,497 B2 * | 3/2015 | Haider | G21K 1/10 378/147 |
| 8,971,498 B2 * | 3/2015 | Haider | G21K 1/10 378/147 |
| 9,183,961 B2 * | 11/2015 | Fadler | G21K 1/10 |
| 2010/0104064 A1 | 4/2010 | Zelakiewicz et al. | |
| 2011/0291012 A1 | 12/2011 | Takahashi et al. | |
| 2012/0025092 A1 | 2/2012 | Zelakiewicz et al. | |
| 2012/0205518 A1 | 8/2012 | Voutilainen et al. | |

* cited by examiner

RECONFIGURABLE LIQUID ATTENUATED COLLIMATOR

Pursuant to 37 C.F.R. §1.78(a)(4), this application claims the benefit of and priority to prior filed Provisional Patent Application No. 61/817,567 filed 30 Apr. 2013, which is explicitly incorporated herein by reference.

RIGHTS OF THE GOVERNMENT

The invention described herein may be manufactured and used by or for the Government of the United States for all governmental purposes without the payment of any royalty.

FIELD OF THE INVENTION

The present invention relates generally radiographic imaging hardware and methods, and more specifically, to a collimator and mask apparatus and related methods for enhancing captured image quality.

BACKGROUND OF THE INVENTION

In the field of x-ray and gamma-ray detection and imaging, it is known that lens structures are ineffective for focusing highly energetic photons. As a result, when detection or imaging of an X-ray or gamma-ray source is desired, other techniques must be used to scale the target emissions to an appropriate detector. For example, a pinhole collimator may be used to constrain energetic photons of the target to an image detector. In such configurations, a small hole is drilled through a high-Z material. The pinhole collimator is disposed between the target and the detector at a suitable distance from the detector. Emissions from the target pass through the penetration in the pinhole collimator, and an inverted image of the target is exposed upon detector. It is noted that decreasing the pinhole diameter yields increased spatial resolution. However, since fewer photons reach the detector in a given time, as the pinhole aperture becomes smaller additional exposure time is required to obtain an acceptable image from a given intensity target.

To overcome this limitation, it is possible to use a plurality of pinholes disposed in a high-Z material as noted above. This may be referred to as a coded aperture mask. This increase in pinhole aperture area yields a proportional increase in the number of photons received by the detector in a given period of time. Therefore the exposure duration may be reduced for a given target in this configuration. However, the coded aperture necessarily projects a plurality of overlapping images onto the detector. Computer executed algorithms may be performed to unify the plurality of projected images captured by the detector. Unfortunately, inherent noise associated with the plurality of pinholes' placement, and transient signals from the detector, tend to produce unacceptable amounts of distortion and blur.

It has been observed that imaging the same target with a variety of physically different masks, or apparently different (presented to the target and detector in a different orientation) masks, allows effective noise reducing techniques to be employed. When a given target is imaged with a plurality of different coded apertures, the data corresponding to the target will be readily identifiable, while the data corresponding to inherent noise will change from mask configuration exposure to a different mask configuration exposure. Such noise may then be effectively identified and excluded.

Some systems use a plurality of tungsten or lead plates that are selectively interchanged for each imaged exposure. Other systems translate or rotate the mask with respect to the image and detector. However, each of those techniques yields a relatively small number of distinct patterns. Moreover, the pre-established patterns may not be readily reconfigured to assist in the imaging under particular environmental and target orientation conditions.

Despite the current advances in X-ray and gamma-ray imaging systems and techniques, there remains a need for apparatus and methods of improved imaging of a radioactive target with a fully reconfigurable coded aperture mask, buy use of a reconfigurable liquid attenuated collimator apparatus.

SUMMARY OF THE INVENTION

The present invention overcomes the foregoing problems and other shortcomings, drawbacks, and challenges of imaging radioactive objects, targets, and sources. While the invention will be described in connection with certain embodiments, it will be understood that the invention is not limited to these embodiments. To the contrary, this invention includes all alternatives, modifications, and equivalents as may be included within the spirit and scope of the present invention.

In one embodiment of the disclosed invention, a reconfigurable radiographic aperture mask apparatus is provided. The apparatus includes a body portion configured to receive an attenuating liquid having a first attenuation value per unit volume. The apparatus further includes a grid portion mated to a face of the body portion and a plurality of passageways each having a cross sectional area and a length. The plurality of passageways is disposed within the grid portion. A plurality of plugs is slidably disposed within the plurality of passageways, and each of the plurality of plugs has a second attenuation value per unit volume less than the first attenuation value. One of the plurality of passageways is filled with a column of attenuating liquid that is coincident with an end of the one of a plurality of plugs contained therein, and wherein the column substantially conforms to the cross sectional area.

A variably reconfigurable radiographic aperture mask apparatus is provided. The apparatus includes a grid manifold having an end cap and a plurality of passageways. Each passageway has a cross sectional area and a length. The plurality of passageways is disposed within the grid manifold, and the end cap is fabricated from a material having a first attenuation value per unit volume. A plurality of conduits is fluidically coupled to the plurality of passageways. A pumping system includes a pump and a control logic. The pumping system is fluidicically coupled to the plurality of conduits and configured to pump an attenuating liquid having a second attenuation value per unit volume into the plurality of conduits and the plurality of passageways. The first attenuation value is less than the second attenuation value. The attenuating liquid forms a column that substantially conforms to the cross sectional area of one of the plurality of passageways or a cooperating one of a plurality of conduits, and terminates at a position along the length of the one of the plurality of passageways or the cooperating one of a plurality of conduits.

In another embodiment of the disclosed invention a method of variably configuring a radiographic aperture mask is provided. The method includes providing a plurality of passageways each having a cross sectional area and a length. The method also includes determining a desired attenuation to be assigned to one of the plurality of passageways, and introducing or evacuating a column of an attenuating liquid that substantially conforms to the cross sectional area into the one of the plurality of passageways. The method further includes terminating the column of the attenuating liquid at a position along the length of the one of a plurality of passageways. The composition of the attenuating liquid, the length of the column of attenuating liquid, and the terminating position produce the desired attenuation.

Additional objects, advantages, and novel features of the invention will be set forth in part in the description which follows, and in part will become apparent to those skilled in the art upon examination of the following or may be leaned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Figure 1:
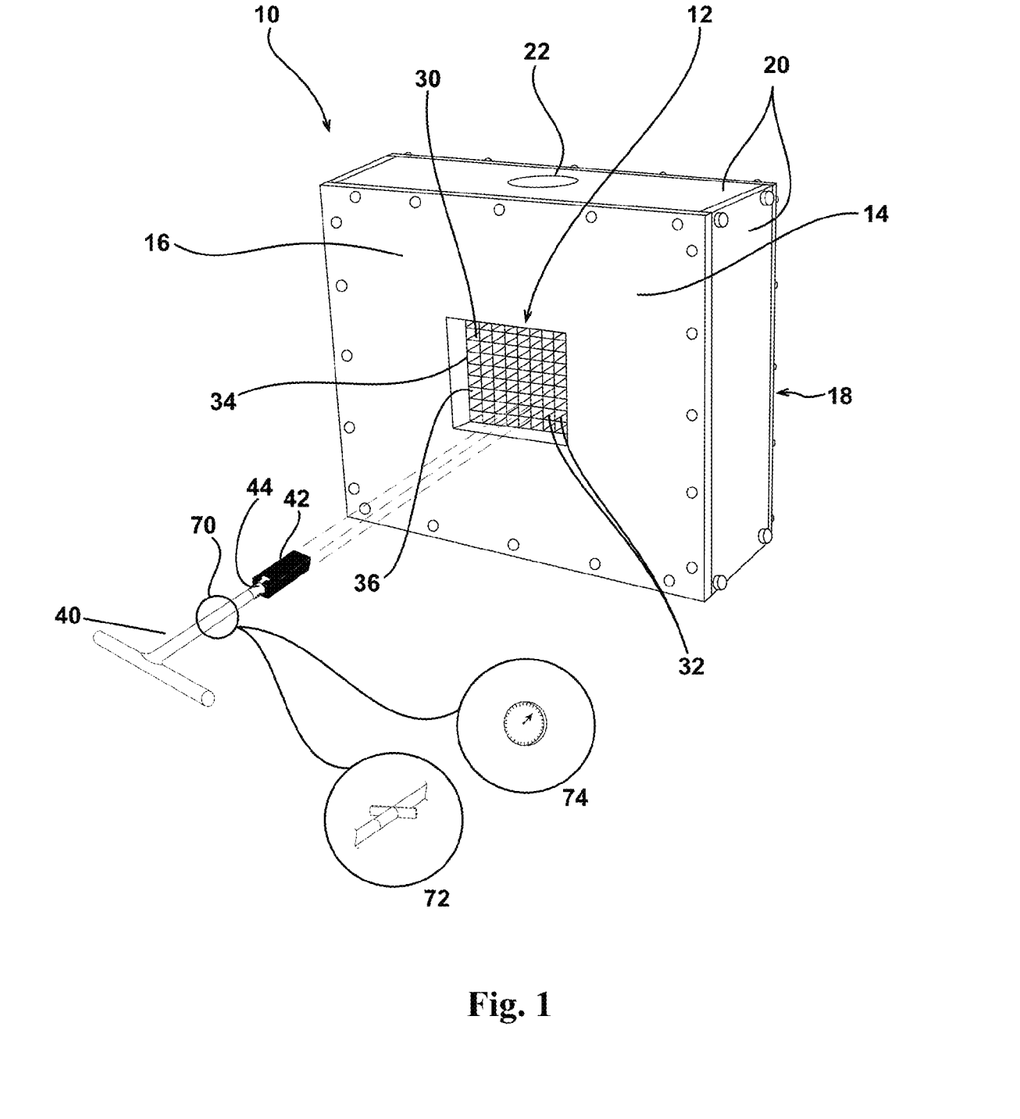
FIG. 1 is an isometric illustration of one embodiment of the disclosed collimator.

FIG. 1, is a perspective view of the fully reconfigurable liquid attenuated collimator 10 is shown. The collimator 10 includes a grid portion 12 and a body portion 14. The body portion 14 is a three dimensional container having a liquid tight internal volume configured for receiving an attenuating liquid. The body 14 includes a front plate 16, a back plate 18, and a plurality of side plates 20. In the illustrated embodiment, the body portion 14 is approximately a rectangular prism, but other configurations may produce acceptable results. In some embodiments of the disclosed invention, a port 22 is provided to facilitate introduction of the attenuating liquid into the internal volume of the body portion 14. A drain (not shown), may also be included to assist in evacuating attenuating liquid from the body portion 14. In the alternative, a vacuum driven or siphon apparatus may be used to withdraw attenuating liquid from internal volume using the port 22.

The grid portion 12 includes a plurality of dividing walls 30. The dividing walls 30 in the depicted embodiment of FIG. 1 form a plurality of square prismatic passageways 32, but other cross-sectional geometries, to include circle, hexagon, rhombus, and others may be used. The grid structure 12 may be disposed within the volume of the body portion 14 such that the grid portion 12 is coincident with, and orthogonal to, the inside face 34 of the front plate 16. The perimeter wall 36 of the grid portion 12 is bonded to form a liquid-tight interface between the grid portion 12 and the inside face 34 of the front plate 16.

In the depicted embodiment as shown in FIG. 1, attenuating liquid added via the port 22 would begin to fill the internal volume of the body portion 14. The liquid level would rise until reaching the bottom of the perimeter wall 36 of the grid portion 12. If additional liquid is added, it would begin to spill out of the passageways 32 at the bottom of the grid portion 12. Therefore, to complete the liquid-tight integrity of the collimator 10, and to establish a means for full reconfiguration of the grid portion 12, liquid tight plugs 38 are inserted in each of the passageways 32. The plugs 38 are configured to establish an interference fit within the passageways 32 while allowing the plugs 38 to be selectively pushed or pulled along the length of the passageway 32. The degree of interference fit between the plugs 38 and passageways 32 will vary with the viscosity of the attenuating liquid. As the liquid's viscosity increases, the interfaces between the plugs 38 and dividing walls 30 are less likely to permit liquid leakage In another embodiment of the disclosed invention, the plug 38 itself may alternatively be a clearance fit with respect to the passageway 32. O-rings, flanges, or other sealing features may be employed to establish a liquid tight seal between the plug 38 and the passageway 32.

The plugs 38 may be fabricated from a material that possesses low emission attenuation properties and is sufficiently thermally stable so as to maintain liquid tight integrity (as well as selectable freedom of motion within the passageway 32) throughout the range of operating temperatures. If thermal expansion characteristics between the material of the dividing walls 30 and the plugs 38 are too dissimilar, leaking or binding may occur at operating temperatures. One suitable material for fabrication of the plugs 38 is Polyether Ether Ketone (PEEK).

Operation of the collimator 10 depends upon sufficient dissimilarity between the degree of attenuation provided by the attenuating liquid and the degree of attenuation provided by the structures used to constrain the attenuating liquid in the region to be radiographically imaged. In an ideal system, the plugs 38 would provide no attenuation. In such an ideal system, attenuation would be only established by the quantity of attenuating liquid present. In a typical system, attenuation in a given region is equal to the sum of a fixed value (representative of the plug 38 or other supporting structure), plus the attenuation of the attenuating liquid in that region.

For example, a low-Z or low attenuation material may be defined as one with a Z value of 6 or less. Also, for the purposes of using the collimator 10 for radiographic imaging, a material having a Z value of about 10 or less may be deemed to be substantially transparent to radiographic emissions. In general, acceptable results may be obtained from attenuating liquids having a Z value greater than about 25, where the Z of iron is 26. The most beneficial known Z value is 80 (or more), where 80 is the Z value of mercury. It should be noted that that the term "first attenuation value" and "second attenuation value" may be used herein to compare the relative attentions of liquids and structures. Furthermore, the material density affects the attenuation values. For example, the Z value of air and plastic is roughly equivalent, but the photons will penetrate through the air much more effectively. In general, for a photon of some energy, the mean free path in the attenuator liquid must be no more than half that of the remainder of the imaging portion of the device. Ideally, the mean free path in the attenuator liquid would be no more than one tenth of that of the remainder of the imaging portion of the device.

A tool 40 is configured to interface with a cooperating feature of the plugs 38. As shown in FIG. 1 a T-slot 42 on the plug 38 cooperates with a T-projection 44 on the tool 40 to temporarily join the tool 40 and the plug 38. Once joined, the tool 40 may be pushed or pulled along the axis of the passageway 32 to relocate the plug 38 within the passageway 32. As will be recognized by one of ordinary skill in the art, the gender of the cooperating features may be reversed. Additionally, other cooperating geometries, also referred to as adjusting features, may be employed, to include threaded bores and shafts, rare earth magnetics, electromagnetics, barbs, cams, and the like. As will be explained in greater detail below, relocating the plug 38 along the passageway 32 will determine the amount of attenuating liquid that occupies the passageway 32. Such manipulation of the plugs 38 will produce maximum attenuation when the plug 38 is disposed nearest the front plate 16, a minimum attenuation value when the plug 38 is disposed nearest the black plate 18, and an intermediate value when the plug 38 is disposed there between.

Several attenuating liquids may produce acceptable results. It has been observed that mercury is very desirable from a functional standpoint because t is liquid at room temperature and has relatively high density and attenuation capabilities. However, due to its relatively high toxicity, substantial precautions must be taken to isolate the mercury from users and from introduction into the environment. Several alloys are available, but they generally require the use of a heating source to remain in the liquid state. One acceptable eutectic alloy includes 50% bismuth, 26.7% lead, 13.3% tin, and 10% cadmium, by weight, with a melting point of approximately 70 degrees Celsius. It may be obtained from AIM Specialty Materials under the trade name of AIM-70. Additionally, another alloy, denoted by the trade name AIM-47 from the same supplier, includes 47.7% bismuth, 22.6% lead, 8.3% tin, 5.3% cadmium, and 19.1% indium by weight, with a melting point of approximately 47 degrees Celsius. AIM-47 also has good attenuating qualities, but exhibits less than half of the expansion upon solidification as experienced with AIM-70. AIM 47 expands 0.0002 inches per inch over the first 6 minutes, followed by shrinkage to −0.0002 inches per inch thereafter. This reduced expansion is desirable to minimize potentially damaging stresses on the dividing walls 30 if the attenuating liquid is permitted to solidify within the collimator 10.

Figure 2:
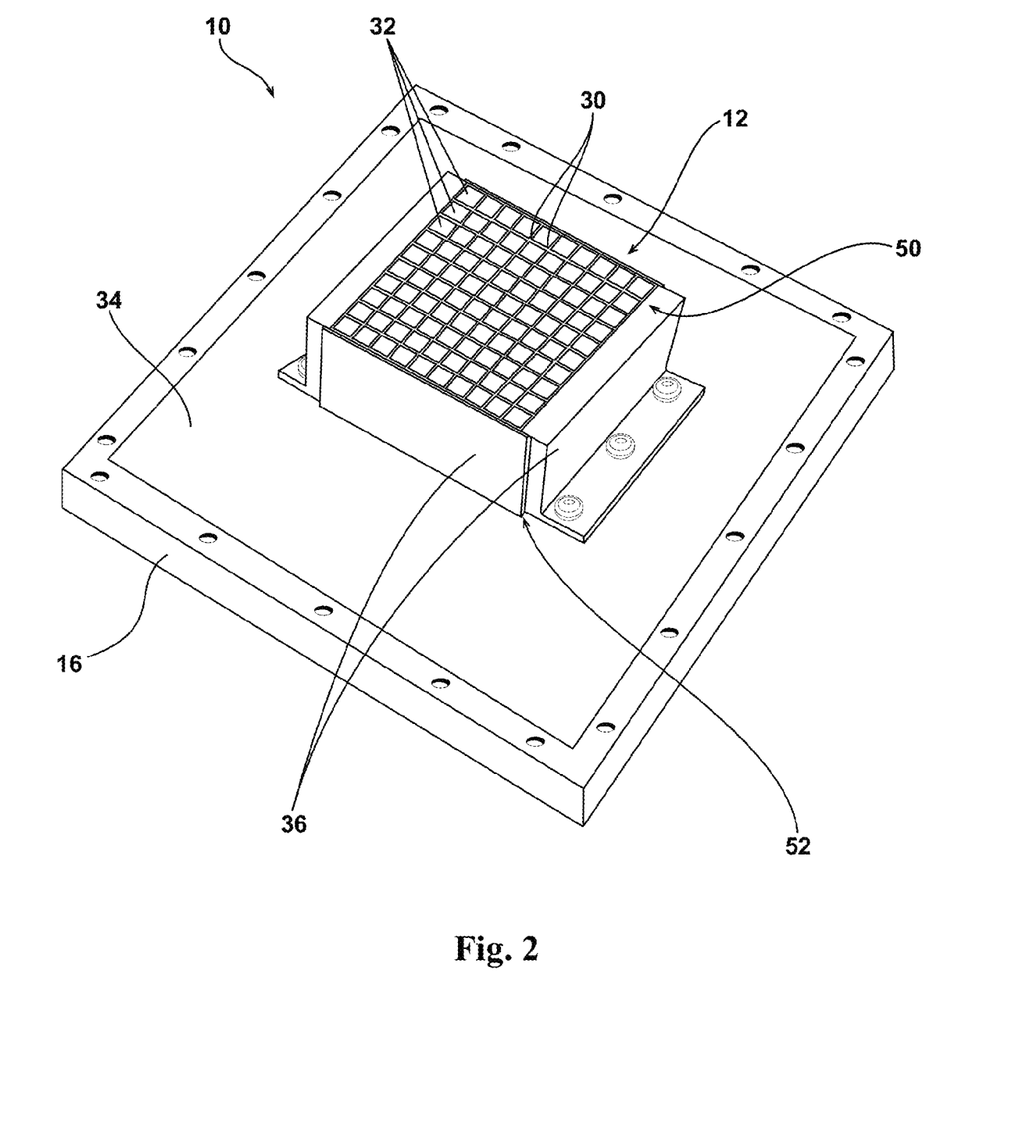
FIG. 2 is an isometric illustration of the rear portion of the rear face of an embodiment of the disclosed invention.

Turning now to FIG. 2, a rear view of the front plate 16 is shown. This view exposes the inner face 34 that is oriented toward the interior volume of the body portion 14 when assembled. It should be noted that while there is a liquid tight interface between the perimeter wall 36 and the inner face 34 of the front plate 16, clearance exists between the distal end 50 of the grid portion 12 with respect to the back plate 18. When the collimator 10 is assembled with plugs 38 disposed at the distal end 50 of the passageways 32, attenuating liquid introduced into the body portion 14 fills the volume (including the space between the distal end 50 of the grid portion 12 and the back plate 18), but the attenuating liquid does not enter the passageways 32. The back plate may include a region of low attenuation material such as a window (not shown), coincident with the footprint of the grid portion 12. In this distally disposed configuration, the grid portion 12 is collectively at its lowest attenuation level, since attenuating liquid cannot enter the internal volumes of the passageways 32. In this configuration, the attenuation of emissions passing through the grid region 12 of the collimator 10 is reduced only by the sum of the attenuation value of the window, plus the attenuation of the plugs 38, plus the attenuation of the dividing walls 30, and the attenuation resulting from the volume of attenuating liquid between the distal end 50 of the grid region 12 and the window of the back plate 18. Conversely, if the plugs 38 are disposed coincident with the proximal end 52 of the grid region 12, the greatest attenuation value is achieved. Since the aforementioned static component attenuation values remain unchanged, when attenuating liquid is permitted to fill the passageways 32 as a result of the orientation of the plugs 38, total attenuation is increased.

It should be noted, as will be explained in greater detail below, that each plug 38 may be moved independently from each of the other plugs 38. Plugs 38 may be manipulated serially or in parallel, but the position of one plug 38 is not dependent upon the position of any other plug 38. Also, intermediate positions of the plugs 38 (at a position between the distal end 50 and proximal end 52) may be employed. Each of these configuration options enables the collimator 10 to yield a high degree of attenuation variability.

Figure 3:
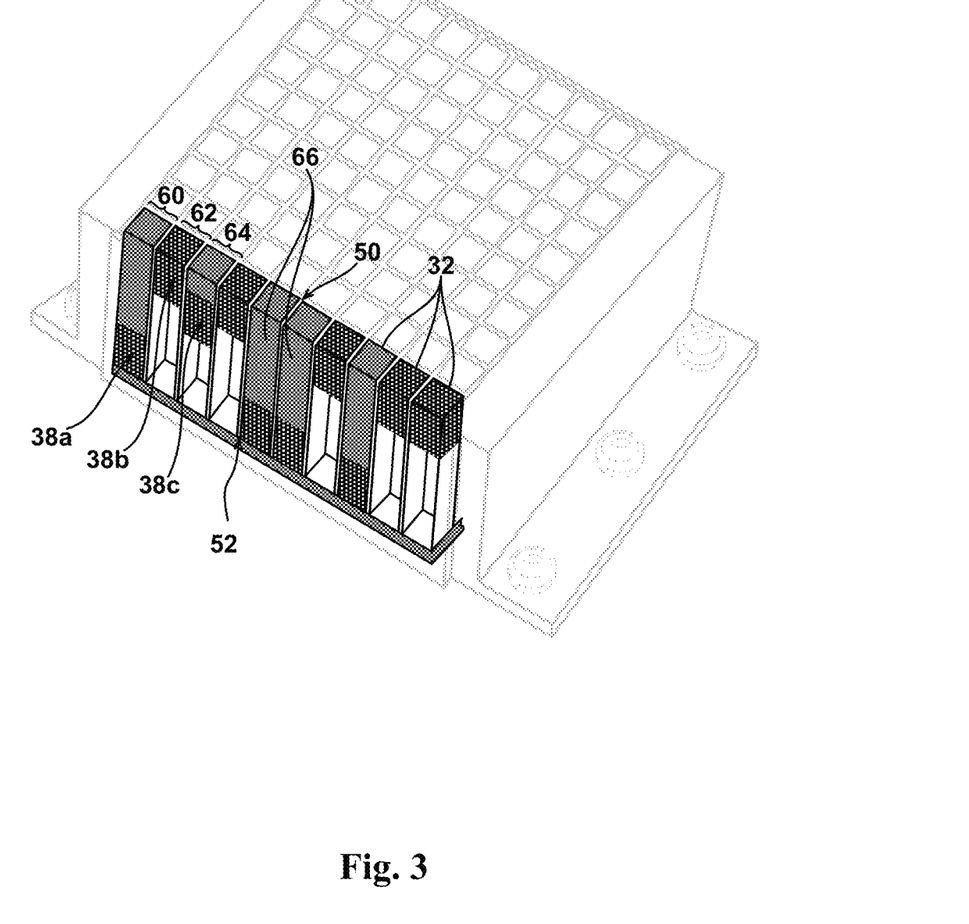
FIG. 3 is an isometric partial cut away illustration of a row of passageways from an embodiment of the disclosed invention.

Turning attention to FIG. 3, a perspective cutaway view of one row of passageways 32 in the grid portion 12 is shown. The passageway 32 at position 60 denotes a configuration wherein the plug 38a is coincident with the proximal end 52 of the grid portion 12. In this configuration, the passageway 32 fills with attenuating liquid 66, and maximum attenuation results. The passageway 32 at position 62 denotes a condition wherein the plug 38b is coincident with the distal end 50 of the grid portion 12. In this configuration, all attenuating liquid 66 is driven out of the passageway 32, and minimum attenuation occurs. Lastly, the passageway 32 at position 64 is in a configuration wherein approximately 75% of the attenuating liquid 66 is displaced from the passageway 32 by the plug 38c, and an intermediate degree of attenuation occurs.

Various techniques known to one of ordinary skill in the art may be used to select from discrete or infinitely variable positions of the plugs 38. For example, and not by way of limitation, the tool 40 of FIG. 1. may employ a depth indicator 70. The depth indicator 70 may be a shoulder 72 or other projection that contacts the proximal end 52 of the dividing walls 30 or other datum point. A plurality of separate tools 40 may be configured with distinct shoulders 72 dimensions. For example, tools 40 may be fashioned with shoulders 72 corresponding to plug 38 positions that result in attenuation of 25%, 50%, and 75%. In another embodiment, the depth indicator 70 may be configured as a dial indicator 74, proximity sensor, vernier scale, or similar structure suitable for indicating the depth of a plug 38 (or corresponding attenuation value). Additional structures may be added to prevent complete withdrawal of the plugs 38 after assembly has been completed (thus preventing the loss of attenuating liquid). In one embodiment, a reconfiguration jig (not shown), consisting of a plate including a plurality of bores dimensioned smaller than the outside dimension of the plugs 38, may be temporarily affixed to the front plate 16 during adjustment of the plugs 38. The tool 40 is passed through the penetrations of the reconfiguration jig, but the plug 38 is prevented from inadvertent withdrawal by the reconfiguration jig. In the alternative, if constructed of sufficiently low attenuation materials, the reconfiguration jig, or similar retraining features, may remain mated to the front plate 16 during normal use.

The previously described collimator 10 enables a user to manually configure the attenuation pattern through the manipulation of plugs 38 that displace attenuating liquid from the passageways 32. In another embodiment, shown as the collimator 10a in FIG. 3, an apparatus for automated reconfiguration of an attenuation pattern is presented.

Figure 4:
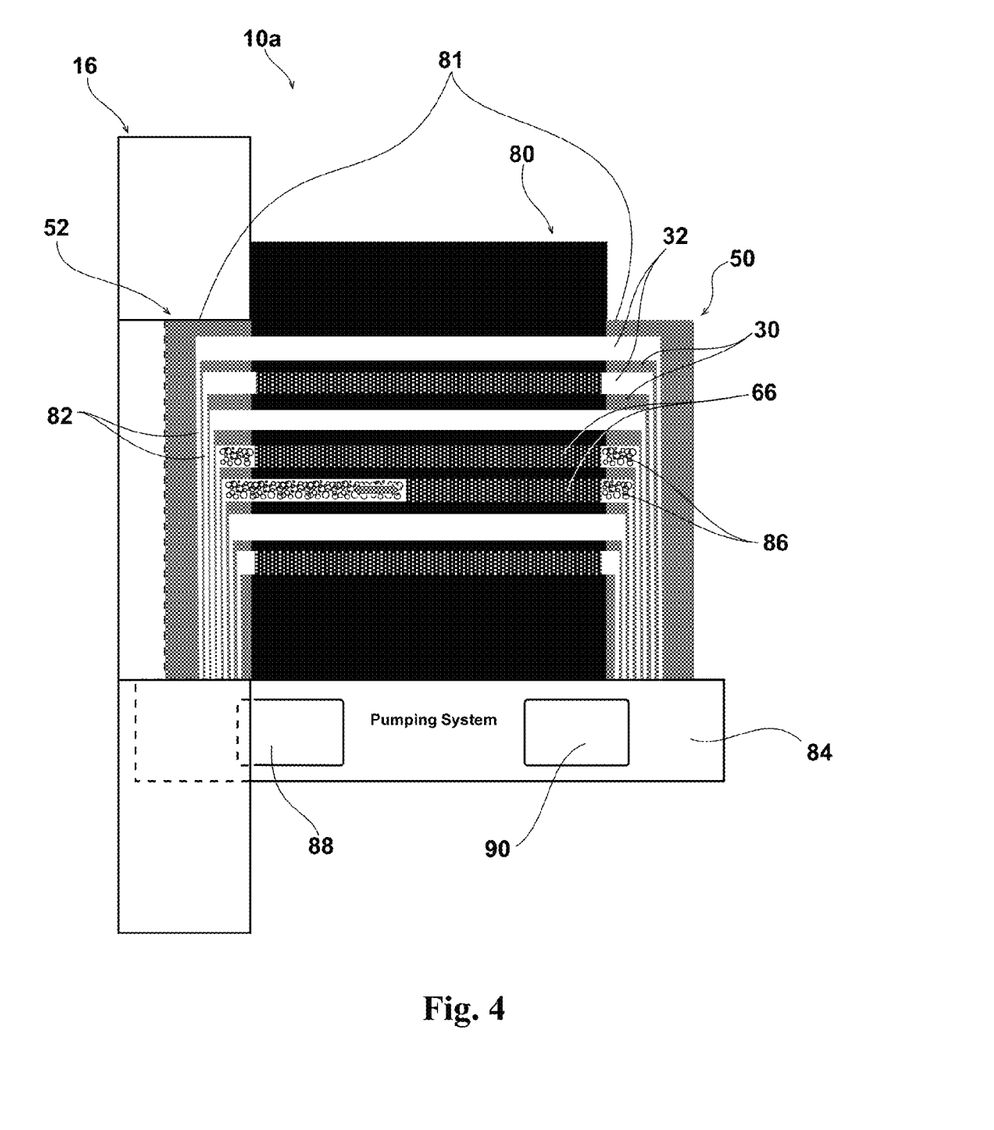
FIG. 4 is a partial cut away side view of an embodiment of the disclosed invention including a pumping system and related interconnecting features.

A grid manifold 80 includes a plurality of conduits 82 fluidically coupled to a plurality of passageways 32. The grid manifold 80 may be fabricated with dividing walls 30 comprised of attenuating material and end caps 81 fabricated from a suitably low attenuating material such as PEEK. The grid manifold 80 may be constructed from a plurality of laminations that are fused together or otherwise joined with gaskets, adhesives, sealants, or the like.

A pumping system 84 may displace attenuating liquid 66 by introduction and evacuation of a gas 86, such as air, nitrogen, argon or the like from the conduits 82 and passageways 32. The collimator 10a emulates the same attenuation variability as previous embodiments that use plugs 38, but the pumping system 84 allows for enhanced capabilities that are unachievable with the collimator 10. For example, real time adjustment of attenuation, while being exposed to radioactive emissions, may be made with exposing a user to dangerous conditions. Additionally, the collimator 10a allow for significantly greater adjustments per unit time than possible when a user manipulates the plugs 38 of the collimator 10.

If a high degree of attenuation is desired in a particular passageway 32, the pumping system may introduce attenuating liquid 66 via a conduit 82 located at the distal end 50 of the grid manifold 80. Once the passageway 32 is completely filled with attenuating liquid 66, maximum attenuation is achieved. Should a variable degree of attenuation be required (or a minimum amount of attenuation), only a portion of the passageway 32 may be filled. Since every isotope emits a unique set of gamma ray energies, by adjusting the amount of attenuation over time, it is possible to deduce the type of isotope being imaged. Furthermore, by modulating the liquid attenuator in the device, an image can be reconstructed even with only a single, non-imaging detector, as opposed to an industry standard imaging detector.

In some embodiments, a charge of gas 86 may be introduced adjacent the attenuating liquid 66 to purge the conduit 82 of attenuating liquid 66. This prevents the pathways of the conduits 82 from serving as a source of significant attenuation. In other embodiments, the conduits 82 are dimensioned sufficiently thin, so as to provide negligible attenuation. In yet other embodiments, attenuating liquid 66 is maintained in the conduits 82 so as to provide a consistent degree of attenuation that may be compensated for via noise reduction and image reconstruction algorithms.

In order to maintain consistent and repeatable attenuation, attenuating liquid 66 should be introduced as a column that substantially conforms to the interior walls of the passageways 32. If the passageways 32 are oriented horizontally, low viscosity attenuating liquids 66 may undesirable settle to the bottom of the passageway 32, leaving a void above the attenuating liquid. This condition may be cured by introducing a sufficient pressure of gas 86 on both sides of the column of attenuating liquid 66. The length of the column, the composition of the attenuating liquid 66, and the position along the length of the passageway 32 at which the column terminates, will all factor into the realized attenuation level.

The pumping system 84 may include a plurality of pumps 88, to include peristaltic, screw, lobe, gear, rotary vane, reciprocating, piston, diaphragm, or other suitable means for displacing liquid or gas 86 in a controlled manner. In some embodiments, each conduit 82 is coupled to a dedicated pump 88, while other embodiments use a plurality of valves and gates to couple a plurality of conduits 82 to a signal pump 88. Control logic 90 receives commands from a user, and displaces or introduces the attenuating liquid 66 in response thereto. Some embodiments may include sensors or feedback loops to make continued adjustments to maintain a desired degree of attenuation during use. In yet other embodiments, the control logic 90 and sensors cooperate to make adjustments to the attenuation of the coded aperture mask of the grid manifold 80 in response to signals received by an X-ray or gamma-ray detector. For example, a radiative target's emissions may be passed through a first coded aperture mask of the grid manifold 80 onto a detector. In response from signals received from the detector, the control log may reconfigure the grid manifold 80 into a second (and subsequent) coded mask to improve the quality of image reconstruction capabilities during subsequent exposures.

The length of attenuator in a given column affects the optimal image reconstruction method used, where longer columns favor iterative, forward-model-based methods and shorter columns allow for more traditional methods. In addition to the distance between the device and the detector, the ratio between the length and the width of a given column, as well as the spacing between columns, affects the degree of multiplexing utilized. Here greater multiplexing means that the images from adjacent columns overlap a greater amount. Higher multiplexing results in faster acquisition times at the expense of image quality and vice versa. These parameters may be adjusted based on the application.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A variably reconfigurable radiographic aperture mask collimator apparatus, the apparatus comprising:
    a grid manifold having an end cap and a plurality of passageways each having a cross sectional area and a length, wherein the plurality of passageways is disposed within the grid manifold, and wherein the end cap is fabricated from a material having a first attenuation value per unit volume;
    a plurality of conduits fluidically coupled to the plurality of passageways;
    a pumping system having a pump and a control logic, wherein the pumping system is fluidicically coupled to the plurality of conduits and configured to pump an attenuating liquid having a second attenuation value per unit volume into the plurality of conduits and the plurality of passageways;

wherein the first attenuation value is less than the second attenuation value;

wherein the attenuating liquid forms a column that substantially conforms to the cross sectional area of one of the plurality of passageways or a cooperating one of a plurality of conduits, and terminates at a position along the length of the one of the plurality of passageways or the cooperating one of a plurality of conduits; and wherein the attenuating liquid is present in the one of a plurality of passageways, and absent from a corresponding one of a plurality of conduits.

\* \* \* \* \*